(12) United States Patent
Alibeyli et al.

(10) Patent No.: US 11,130,118 B2
(45) Date of Patent: Sep. 28, 2021

(54) PREPARATION OF NATURAL ZEOLITE CATALYST AND THE METHOD OF PRODUCING DIMETHYL ETHER FROM METHYL ALCOHOL USING THIS CATALYST

(71) Applicant: TUBITAK, Ankara (TR)

(72) Inventors: Rafig Alibeyli, Istanbul (TR); Bariş Kiriş, Istanbul (TR); Gamze Behmenyar, Kocaeli (TR); Muzaffer Yaşar, Instanbul (TR); Alper Sarioğlan, Kocaeli (TR); Osman Okur, Kocaeli (TR)

(73) Assignee: TUBITAK, Ankara (TR)

( * ) Notice: Subject to any disclaimer, the term of this patent is extended or adjusted under 35 U.S.C. 154(b) by 0 days.

(21) Appl. No.: 16/760,551

(22) PCT Filed: Nov. 2, 2018

(86) PCT No.: PCT/IB2018/058610
§ 371 (c)(1),
(2) Date: Apr. 30, 2020

(87) PCT Pub. No.: WO2019/087139
PCT Pub. Date: May 9, 2019

(65) Prior Publication Data
US 2020/0276565 A1    Sep. 3, 2020

(30) Foreign Application Priority Data

Nov. 2, 2017 (TR) .................................. 2017/17129

(51) Int. Cl.
| | | |
|---|---|---|
| *B01J 29/70* | (2006.01) | |
| *B01J 37/06* | (2006.01) | |
| *B01J 37/08* | (2006.01) | |
| *B01J 37/30* | (2006.01) | |
| *C01B 39/02* | (2006.01) | |
| *C07C 41/09* | (2006.01) | |

(52) U.S. Cl.
CPC .............. *B01J 29/70* (2013.01); *B01J 37/06* (2013.01); *B01J 37/08* (2013.01); *B01J 37/30* (2013.01); *C01B 39/026* (2013.01); *C07C 41/09* (2013.01); *B01J 2229/16* (2013.01); *B01J 2229/37* (2013.01)

(58) Field of Classification Search
CPC ... B01J 29/70; B01J 37/06; B01J 37/08; B01J 37/30; B01J 2229/16; B01J 2229/37; C01B 39/026; C07C 41/09
See application file for complete search history.

(56) References Cited

U.S. PATENT DOCUMENTS

| | | | | |
|---|---|---|---|---|
| 3,676,330 A | * | 7/1972 | Plank | ..................... C10G 11/05 502/64 |
| 4,595,785 A | | 6/1986 | Brake | |
| 5,506,182 A | * | 4/1996 | Yamagishi | ............. B01J 29/061 502/64 |
| 8,541,630 B2 | | 9/2013 | Guo et al. | |
| 8,957,259 B2 | | 2/2015 | Dagle et al. | |
| 2007/0078285 A1 | | 4/2007 | Dagle et al. | |

FOREIGN PATENT DOCUMENTS

| | | | | |
|---|---|---|---|---|
| CN | 100522813 C | * | 8/2009 | ............. B01J 29/89 |
| RU | 2630675 C2 | * | 9/2017 | ............. B01J 29/65 |

OTHER PUBLICATIONS

Catalysis Communications 6(2) (2005), 147-152 published by Yaripour, F., Baghaei, F., Schmidt, I. B. Perregaard, J., with name "Catalytic Dehydration of Methanol to Dimethyl Ether (DME) Over Solid-Acid Catalyst"—online Jan. 5, 2005.
"Study of the Conversion of Methanol to Dimethyl Ether on Zeolite HZSM-5 Using Situ Flow MAS NMR" published by Lauren K. Carlson, Paul K. Isbester, Eric J. Munson in the "Solid State Nuclear Magnetic Resonance" journal, 16 (1999), p. 93-102—online May 2000.
"Vapour Phase Dehydration of Crude Methanol of Dimethyl Ether Over Na-modified H-ZSM-5 Catalysts" published by V. Vishwanathan, Ki-Won Yun, Yae-Woo Kim, Hyun-Seog Roh in the Applied Catalysts A: General journal, 276 (2004), p. 251-255—online Sep. 11, 2004.
"Dehydration of Methanol to Dimethyl Ether Employing Modified H-ZSM-5 Catalysts" published by Khandan, N., Kazemeini, M., Aghaziarati, M., Ave, A., in the Iranian Journal of Chemical Engineering, 6(1) (2009)—online Winter 2009.
"A new Langmuir-Hinshelwood mechanism for the methanol to dimethylether dehydration reaction over clinoptilolite-zeolite catalyst" published by S.J. Royaee et al. In Applied Catalysis A: General 338 (2008)—online Jan. 20, 2008, pp. 114-120.

* cited by examiner

*Primary Examiner* — Rosalynd A Keys
(74) *Attorney, Agent, or Firm* — Crose Law LLC; Bradley D. Crose

(57) ABSTRACT

The present invention relates to the preparation of various types of natural zeolite catalysts from natural zeolites such as clinoptilolite and the method of producing dimethyl ether from methyl alcohol using these natural zeolite catalysts.

8 Claims, No Drawings

PREPARATION OF NATURAL ZEOLITE CATALYST AND THE METHOD OF PRODUCING DIMETHYL ETHER FROM METHYL ALCOHOL USING THIS CATALYST

TECHNICAL FIELD

The present invention relates to the preparation of various types of natural zeolite catalysts from natural zeolites such as clinoptilolite and the method of producing dimethyl ether from methyl alcohol using these natural zeolite catalysts.

PRIOR ART

In the known state of the art, the method of producing dimethyl ether by dehydration of methyl alcohol is known. According to this method, one molecule of water is separated from two molecules of methyl alcohol to form dimethyl ether:

$$2CH_3OH \rightarrow CH_3OCH_3 + H_2O$$

This method is usually carried out on various solid catalysts with acidic character. Said catalysts are separated into two groups, namely oxide catalysts and artificial zeolite catalysts. Some important studies on the use of these catalysts in the process of dimethyl ether production from methyl alcohol are as follows:

In the article Catalysis Communications 6(2) (2005), 147-152 published by Yaripour, F., Baghaei, F., Schmidt, I. B. Perregaard, J., with name "Catalytic Dehydration of Methanol to Dimethyl Ether (DME) Over Solid-Acid Catalyst", $\gamma$-$Al_2O_3$ and silica-modified $\gamma$-$Al_2O_3$ catalyst is used for the dehydration of methyl alcohol. At atmospheric pressure and a temperature of 300° C., the efficiency of dimethyl ether reaches 58-75% on this catalyst.

United States patent document number US2007078285 refers to the use of $\gamma$-alumina, palladium-doped $\gamma$-alumina, phosphoric acid modified $\gamma$-alumina, and similar acid catalysts or different mixtures thereof as catalysts for the production of dimethyl ether from methyl alcohol. Using these catalysts, 80-90% dimethyl ether yield (in molar basis) is obtained with methyl alcohol dehydration at 200-500° C.

In the United States patent document number U.S. Pat. No. 4,595,785, the usage of various catalysts composed of titanium oxide and aluminum oxide in varying proportions is mentioned. With the catalysts consisting of 1% titanium and 99% aluminum oxide, the concentration of dimethyl ether in the products obtained at 400° C. and 1034 kPa pressure is 57.5%.

As can be seen from the aforementioned prior art documents, the oxide catalysts used for the dehydration of methyl alcohol are mainly $\gamma$-$Al_2O_3$ or mixtures thereof modified with different metals. The most important deficiencies of the said catalysts are the relatively low efficiency of dimethyl ether on them.

In the known state of the art, artificial zeolite catalysts are also widely used for the production of dimethyl ether from methyl alcohol:

In the article named "Study of the Conversion of Methanol to Dimethyl Ether on Zeolite HZSM-5 Using Situ Flow MAS NMR" published by Lauren K. Carlson, Paul K. Isbester, Eric J. Munson in the "Solid State Nuclear Magnetic Resonance" journal, 16 (1999), p. 93-102, it is mentioned that the production method for dimethyl ether from methyl alcohol is carried out on artificial zeolite H-ZSM-5 catalyst at 250° C.

In the article named "Vapour Phase Dehydration of Crude Methanol of Dimethyl Ether Over Na-modified H-ZSM-5 Catalysts" published by V. Vishwanathan, Ki-Won Yun, Yae-Woo Kim, Hyun-Seog Roh in the Applied Catalysts A: General journal, 276 (2004), p. 251-255, it is mentioned that dimethyl ether is produced from methyl alcohol with 94-97% selectivity at a temperature of 230-340° C. and 1 bar pressure on Na-modified H-ZSM-5 catalyst.

In the article named "Dehydration of Methanol to Dimethyl Ether Employing Modified H-ZSM-5 Catalysts" published by Khandan, N., Kazemeini, M., Aghaziarati, M., Ave, A., in the Iranian Journal of Chemical Engineering, 6(1) (2009), it is mentioned that the H-ZSM-5 catalyst modified for Mg, Zr, Zn and similar metals are developed for the dehydration of methyl alcohol. The efficiency of dimethyl ether was measured as 78-94% and selectivity as 68-99% at 350° C. and 100 bar pressure on this catalyst.

United States patent document number U.S. Pat. No. 8,957,259 refers to obtaining dimethyl ether from methyl alcohol with 90% efficiency on H-ZSM-5 catalyst at a temperature of 300° C.

United States patent document no U.S. Pat. No. 8,541,630 refers to the use of artificial zeolite Y and other mesoporous molecular sieves as the dehydration catalyst. The conversion of methyl alcohol on zeolite Y+Beta catalyst was measured as 86% and selectivity to dimethyl was measured as 98%.

CN101182005 numbered patent document discloses a method of preparing hetero-atom molecular sieve specifically titanium-containing zeolite molecular sieve by natural zeolite modification. (Basis of the Amendment: As suggested by the International Searching Authority)

In the article named "A new Langmuir-Hinshelwood mechanism for the methanol to dimethylether dehydration reaction over clinoptilolite-zeolite catalyst" published by S. J. Royaee et al. in Applied Catalysis A: General 338 (2008), the kinetic behavior of a modified clinoptilolite zeolite for the methanol to dimethylether dehydration reaction has been investigated using a differential fixed bed reactor. (Basis of the Amendment: As suggested by the International Searching Authority)

As can be seen from the documents known in the prior art, it is possible to obtain dimethyl ether with higher yield and selectivity from methyl alcohol on artificial zeolite catalysts than on oxide catalysts. The highest dimethyl ether efficiency and selectivity are obtained on H-ZSM-5 catalyst modified by different metals at high pressure (100 bar).

The most disadvantage of artificial zeolite catalysts commonly used in the process of dehydration of methyl alcohol in the state of the art is that the catalyst costs are very high.

BRIEF DESCRIPTION OF THE INVENTION

The aim of this invention is to prepare natural zeolite catalysts which are economically and technologically superior to various types of natural zeolites such as clinoptilolite and have high yield and selectivity and to perform dimethyl ether production by dehydration of methyl alcohol using these catalysts.

DETAILED DESCRIPTION OF THE INVENTION

An objective of this invention is preparing various types of natural zeolite catalyst such as clinoptilolite comprising the steps of; milling natural zeolite; drying the milled natural zeolite; removal of natural zeolite cations and chemical treatment to increase the ratio of $SiO_2:Al_2O_3$; and obtaining a H-natural zeolite catalyst, containing proton as a cation, with a first calcination treatment of the natural zeolite of which cations are removed and has increased ratio of $SiO_2:Al_2O_3$; and then followed by a second calcination treatment obtaining cation free D-natural zeolite catalyst. In the preferred application of the invention, the first calcination treatment is carried out at 350° C. In the preferred application of the invention, the second calcination is carried out at 550° C.

In the preferred application of the invention, chemical processes for removing natural zeolite cations and raising $SiO_2:Al_2O_3$ ratio includes the steps of performing two-stage cation exchange by treating the milled and dried natural zeolite with $NH_4Cl$ solution, dealumination of the natural zeolite with HCl solution, and two-stage cation exchange of natural zeolite with $NH_4Cl$ solution. After each step mentioned above, the chemical processes for removing the natural zeolite cations and raising the $SiO_2:Al_2O_3$ ratio, the natural zeolite is washed and dried.

An exemplary application of the invention wherein clinoptilolite is used to prepare the natural zeolite catalyst is as follows. Clinoptilolite is first milled and fractionated with a particle size range of 500-1500 μm and dried. Clinoptilolite is then subjected to three-step chemical treatments to remove cations such as Na, K in crystal structure of clinoptilolite and to increase the ratio of $SiO_2:Al_2O_3$ in the structure at the same time. In the first step, clinoptilolite is subjected to 2-step cation exchange with $NH_4Cl$ solution, then the dealumination process is applied to clinoptilolite with HCl solution, and finally for removal of $Na^+$ and $K^+$ cations from the clinoptilolite structure at maximum level, the clinoptilolite is again subjected to 2-step cation exchange with the $NH_4Cl$ solution. As a result of these processes, $NH_4^+$-Clinoptilolite containing ammonium cations ($NH_4^+$) is obtained. After each step of the chemical treatment, the clinoptilolite is washed and dried. The washed and dried $NH_4^+$-Clinoptilolite is then subjected to two-step calcination and eventually H-Clinoptilolite catalyst containing proton ($H^+$) as a cation with high catalytic activity and by subjecting H-Clinoptilolite catalyst to calcination D-Clinoptilolite catalyst which is free of cations is obtained. In an alternative application of the invention, catalysts containing different metal cations can be obtained by subjecting the $NH_4^+$-clinoptilolite to the cation exchange with aqueous solutions of various metal salts.

Table 1, Table 2 and Table 3 below show the element contents of the natural zeolite clinoptilolite and the H-Clinoptilolite catalyst and the D-Clinoptilolite catalyst obtained according to the above-mentioned method, respectively.

TABLE 1

Elemental content of natural zeolite clinoptilolite

| Element | % Weight | % Atomic |
|---------|----------|----------|
| O | 42.48 | 57.17 |
| Al | 9.43 | 7.52 |
| Si | 44.44 | 34.07 |
| Cu | 3.19 | 1.08 |
| Zn | 0.46 | 0.15 |

TABLE 2

The element contents of the H-clinoptilolite catalyst obtained by the process subject of the invention

| Element | % Weight | % Atomic |
|---------|----------|----------|
| O | 44.67 | 59.39 |
| Al | 4.08 | 3.21 |
| Si | 47.9 | 36.28 |
| Cu | 3.04 | 1.02 |
| Zn | 0.31 | 0.1 |

TABLE 3

The element contents of the D-clinoptilolite catalyst obtained by the process subject of the invention

| Element | % Weight | % Atomic |
|---------|----------|----------|
| O | 35.14 | 50.04 |
| Al | 4.29 | 3.62 |
| Si | 54.4 | 44.13 |
| Cu | 5.53 | 1.98 |
| Zn | 0.65 | 0.23 |

As can be seen from the above tables, when the Si:Al ratio of the natural zeolite clinoptilolite is 4.71, this ratio is 11.74 in the H-clinoptilolite catalyst and 12.28 in the D-Clinoptilolite catalyst that are obtained by the method subject of invention. This, in turn, significantly increases the activity of the acidic sites of natural zeolite.

When the H-clinoptilolite catalyst and the D-clinoptilolite catalyst that are obtained by the process subject of the invention are compared with the artificial zeolite catalysts, one of their important advantages is that no binder is required for pelletization and in this way the catalyst particles prepared on the basis of natural zeolite have high mechanical resistance. This advantage is achieved by grinding the natural zeolite at the beginning of the process subject of invention and separating the fraction having the desired particle size.

The process of the present invention for the production of dimethyl ether by dehydration of methyl alcohol is carried out in an inert gas atmosphere at atmospheric pressure and a temperature range of 250-300° C. using the natural zeolite catalyst obtained by the process having the abovementioned steps. The conversion of methyl alcohol in these conditions varies between 68.3-96.5% and the selectivity to dimethyl ether is≈100% (in moles).

A few examples of the method of obtaining dimethyl ether by dehydration of methyl alcohol are described below:

Example 1

H-Clinoptilolite catalyst and D-Clinoptilolite catalyst were prepared according to the method described above for the production of dimethyl ether by dehydration of methyl alcohol. For this purpose; 10 g of clinoptilolite having particle sizes of 500-1000 μm were dried for 6 to 8 hours at 110-130° C. in the air environment. The clinoptilolite was then subjected to 2-step cation exchange with $NH_4Cl$ aqueous solution. Both cation exchange steps were carried out for 6 to 8 hours in a continuous mixing environment at a temperature range of 80-90° C. After the second-stage cation exchange, the clinoptilolite was washed with water and air-dried for 2 to 4 hours at a temperature of 110 to 130° C. Clinoptilolite was then subjected to dealumination treatment in the HCl aqueous solution at a temperature of 70° C. to 90°

C. for 4 to 6 hours in a continuous mixing environment. The clinoptilolite was then washed with water and dried in the air at a temperature of 110 to 130° C. for 2 to 4 hours. Later the clinoptilolite was subjected to 2-step cation exchange with NH$_4$Cl aqueous solution for 2 to 4 hours in a continuous mixing environment at a temperature range of 80-90° C. After that the clinoptilolite was washed with water and dried at 120° C. for 2 to 4 hours in air. Finally, H-clinoptilolite catalyst is obtained by subjecting clinoptilolite to calcination treatment at 350° C. for 2 to 4 hours. And D-clinoptilolite catalyst is obtained by subjecting a certain amount of the H-clinoptilolite catalyst to calcination at 550° C. for 2 to 4 hours in air.

3 g (~3 cm$^3$) of the prepared H-Clinoptilolite catalyst was taken and was used in the dehydration process of methyl alcohol. The said dehydration process was carried out in a continuous laboratory experimental system, having tubular fixed bed steel reactor with a diameter of 10 mm and a length of 200 mm under a nitrogen atmosphere. For this purpose, the H-Clinoptilolite catalyst was activated with N$_2$ gas for 2 hours at 300° C. in atmospheric pressure.

Dehydration was carried out at atmospheric pressure, at a temperature of 300° C., at a flow rate of 0.25 cm$^3$/min (5 hours$^{-1}$) with respect to liquid methyl alcohol and at a flow rate of approximately 11500 hours$^{-1}$ with respect to nitrogen gas. The results are as follows:

CH$_3$OH conversion: % 94.5
Selectivity according to dimethyl ether: % 99.6 (in moles)

Example 2

The catalyst used for the dehydration process and other conditions were the same as in Example 1 at a temperature of 250° C. and results are as follows:

CH$_3$OH conversion: % 68.5
Selectivity according to dimethyl ether: % 99.9 (in moles)

Example 3

Dehydration was carried out at 350° C. using the D-Clinoptilolite catalyst with the other conditions being the same as in Examples 1 and 2 and results are as follows:

CH$_3$OH conversion: % 90.7
Selectivity according to dimethyl ether: % 99.3 (in moles)

Example 4

Dehydration was carried out in the same manner as in Example 2 except that the raw material flow rate was 0.125 cm$^3$/min (2.5 hours$^{-1}$) and results are as follows:

CH$_3$OH conversion: % 84.7
Selectivity according to dimethyl ether: % 99.4 (in moles)

Example 5

The dehydration process was carried out at 350° C. so that the raw material flow rate was 0.50 cm$^3$/min (10 hours$^{-1}$), the same as in Example 3 and results are as follows:

CH$_3$OH conversion: % 78.7
Selectivity according to dimethyl ether: % 99.8 (in moles)

Around these basic concepts, it is possible to develop a wide variety of applications relating to the invention "The Preparation Of Natural Zeolite Catalyst And The Method Of Producing Dimethyl Ether From Methyl Alcohol Using This Catalyst" and the invention cannot be limited to the examples mentioned herein, it is exactly as specified in the claims.

The invention claimed is:

1. A preparation method of natural zeolite catalyst for use in production of dimethyl ether by dehydration of methyl alcohol, characterized in that process steps of;
   a) milling natural zeolite to a particle size range of 500-1500 μm,
   b) drying the milled natural zeolite for 6 to 8 hours at 110-130° C.,
   c) chemical treatment for removal of natural zeolite cations and to increase the ratio of SiO$_2$:Al$_2$O$_3$ comprising following steps;
      performing a two-stage cation exchange with a NH$_4$Cl solution on the dried milled natural zeolite,
      dealumination of the natural zeolite with a HCl solution,
      performing two-stage cation exchange to the natural zeolite with NH$_4$Cl solution,
   d) obtaining a H-natural zeolite catalyst containing proton as a cation with a first calcination treatment of the natural zeolite of which cations are removed and has increased ratio of SiO$_2$:Al$_2$O$_3$,
   e) obtaining a cation free D-natural zeolite catalyst by a followed second calcination treatment of a H-natural zeolite catalyst
   wherein the first calcination treatment in step d) is carried out at 350° C., and
   the second calcination treatment in step e) is carried out at 550° C.

2. The method according to claim 1 wherein the natural zeolite is washed and dried after each sub-step in subjecting to chemical treatment for removal of natural zeolite cations and raising SiO$_2$:Al$_2$O$_3$ ratio.

3. The method according to claim 1, wherein the natural zeolite is clinoptilolite.

4. A method for the production of dimethyl ether by dehydration of methyl alcohol, wherein it is carried out in an inert gas atmosphere at atmospheric pressure and a temperature range of 250-300° C. using at least one of the natural zeolite catalyst obtained by the method according to the claim 3.

5. The method for the production of dimethyl ether by dehydration of methyl alcohol according to claim 4, wherein it is carried out in an inert gas atmosphere at atmospheric pressure and a temperature range of 250-300° C. by using H-Clinoptilolite catalyst.

6. The method for the production of dimethyl ether by dehydration of methyl alcohol according to claim 4, wherein it is carried out in an inert gas atmosphere at atmospheric pressure and a temperature range of 250-300° C. by using D-Clinoptilolite catalyst.

7. The method for the production of dimethyl ether by dehydration of methyl alcohol according to claim 4, wherein it is carried out in flow rate of 0.125 to 0.50 cm$^3$/min range with regard to liquid methyl alcohol.

8. A method according to claim 1 to prepare zeolite catalyst from natural clinoptilolite characterized with steps of;
   a) milling natural clinoptilolite to a particle size range of 500-1500 micron,
   b) drying the milled natural clinoptilolite at 110-130° C. for 6-8 hours in the air environment,
   c) chemical treatment for removal of natural clinoptilolite cations and to increase the ratio of SiO$_2$:Al$_2$O$_3$ comprising following steps;
      performing a two-stage cation exchange with a NH$_4$Cl solution on the dried milled natural clinoptilolite for 6-8 hours at a temperature range of 80-90° C. in a continuous mixing environment, washing with water and air-drying for 2-4 hours at 110-130° C.;

dealumination of the natural zeolite with a HCl solution at 70-90° C. for 4-6 h in a continuous mixing environment, washing with water and air-drying for 2-4 hours at 110-130° C.;

performing two-stage cation exchange to the natural zeolite with $NH_4Cl$ solution for 2-4 hours at 80-90° C. in a continuous mixing environment;

washing with water and air-drying for 2-4 hours at 120° C.;

d) obtaining a H-natural zeolite catalyst containing proton as a cation with a first calcination treatment of the natural zeolite of which cations are removed and has increased ratio of $SiO_2:Al_2O_3$, e) obtaining a cation free D-natural zeolite catalyst by a followed second calcination treatment of a H-natural zeolite catalyst, wherein the first calcination treatment in step d) is carried out at 350° C. for 2-4 h, and the second calcination treatment in step e) is carried out at 550° C. for 2-4 h.

* * * * *